(12) United States Patent
Sugawara

(10) Patent No.: US 7,569,026 B2
(45) Date of Patent: Aug. 4, 2009

(54) METHOD OF PRODUCING BLOOD PROCESSING CIRCUITS AND FILTER UNIT

(75) Inventor: Hiroyuki Sugawara, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 10/574,201

(22) PCT Filed: Sep. 29, 2004

(86) PCT No.: PCT/JP2004/014203

§ 371 (c)(1),
(2), (4) Date: Mar. 31, 2006

(87) PCT Pub. No.: WO2005/032619

PCT Pub. Date: Apr. 14, 2005

(65) Prior Publication Data

US 2007/0043317 A1  Feb. 22, 2007

(30) Foreign Application Priority Data

Oct. 2, 2003  (JP)  ............................. 2003-344752

(51) Int. Cl.
*A61M 37/00* (2006.01)
*A61M 1/00* (2006.01)
*A61B 19/00* (2006.01)

(52) U.S. Cl. ...................... 604/6.09; 604/6.15; 604/318; 604/406; 604/408; 422/44

(58) Field of Classification Search ................ 604/4.01, 604/5.01, 6.09, 6.15, 6.16, 403, 406, 408, 604/410; 210/194, 196, 232, 233, 234; 422/44
See application file for complete search history.

(56) References Cited

U.S. PATENT DOCUMENTS

| | | | | |
|---|---|---|---|---|
| 4,369,779 A | * | 1/1983 | Spencer | ....................... 604/29 |
| 4,596,657 A | * | 6/1986 | Wisdom | ..................... 210/206 |
| 4,985,153 A | | 1/1991 | Kuroda et al. | |
| 4,997,577 A | * | 3/1991 | Stewart | ....................... 210/767 |
| 5,089,146 A | * | 2/1992 | Carmen et al. | .............. 210/782 |
| 5,156,701 A | | 10/1992 | Spencer et al. | |

(Continued)

FOREIGN PATENT DOCUMENTS

JP  5-501368  3/1993

(Continued)

*Primary Examiner*—Leslie Deak
*Assistant Examiner*—Adam Marcetich
(74) *Attorney, Agent, or Firm*—Buchanan Ingersoll & Rooney PC

(57) ABSTRACT

A bag connection comprises a first bag, a tube having a blood-drawing needle at the front end, a plurality of second bags, tubes for connecting the first and second bags, and tubes and branch connectors for connecting the second bags to each other. On the other hand, a filter unit includes a filter, and a tube connected at opposite ends thereof to the inlet and outlet of the filter. The tubes of the bag concatenation and the tube of the filter unit have respective markers attached thereto. With these markers used as marks, both tubes are aseptically connected by a tube aseptic connection device, thereby incorporating the filter unit into an intermediate portion of a tube of the bag concatenation.

26 Claims, 9 Drawing Sheets

U.S. PATENT DOCUMENTS

| | | | |
|---|---|---|---|
| 5,180,504 A * | 1/1993 | Johnson et al. | 210/767 |
| 5,269,946 A * | 12/1993 | Goldhaber et al. | 210/767 |
| 5,496,302 A * | 3/1996 | Minshall et al. | 604/410 |
| 5,601,730 A * | 2/1997 | Page et al. | 210/806 |
| RE35,804 E | 5/1998 | Stewart | |
| 5,779,666 A * | 7/1998 | Teirstein | 604/507 |
| 5,802,689 A * | 9/1998 | Sano | 29/33 T |
| 6,733,433 B1 * | 5/2004 | Fell | 494/37 |
| 7,048,709 B2 * | 5/2006 | Goudaliez et al. | 604/6.09 |
| 2003/0146170 A1 * | 8/2003 | Corbin et al. | 210/739 |
| 2003/0150793 A1 * | 8/2003 | Verpoort et al. | 210/489 |
| 2005/0082218 A1 * | 4/2005 | Verri et al. | 210/436 |
| 2006/0086666 A1 * | 4/2006 | Mari et al. | 210/645 |

FOREIGN PATENT DOCUMENTS

| | | |
|---|---|---|
| JP | 5-116221 | 5/1993 |
| JP | 6-59304 | 8/1994 |
| JP | 2952433 | 7/1999 |
| JP | 2001-276181 | 10/2001 |
| WO | 91/04088 | 4/1991 |

* cited by examiner

METHOD OF PRODUCING BLOOD PROCESSING CIRCUITS AND FILTER UNIT

TECHNICAL FIELD

The present invention relates to a method for assembling a blood treatment circuit which is designed to treat blood collected from a donor. It relates also to a filter unit.

BACKGROUND ART

There is known a blood bag system for centrifugal separation of whole blood collected from a donor into three kinds of blood cell products for blood transfusion, which include concentrated red blood cell (CRC), platelet concentrated (PC), and platelet-poor plasma (PPP).

Such blood cell products for blood transfusion often undergo, after separation and storage, a process of removing white blood cells immediately before transfusion into a patient in order to avoid side effects induced after blood transfusion by contamination with white blood cells.

However, it is known that blood obtained by blood donation gives high-quality blood cell products for blood transfusion if it is freed of white blood cells before separation and storage. In order to remove white blood cells before blood separation and storage, there has been developed a leukocyte removing filter system (in-line filter) consisting of a blood bag system and a filter which are integrally connected to each other. (See Patent Document 1 below.)

However, the system disclosed in Patent Document 1 has the following disadvantages.

First, the in-line filter is inconvenient to handle and makes the system bulky as a whole, although it functions as a constituent of the closed system in which the circuit, filter, and bag are so connected as to permit aseptic blood treatment.

Second, the system has to be discarded together with an intact in-line filter when collected blood is judged to be inadequate for blood products for quantitative or qualitative reasons and hence is discarded. This wastes the in-line filter.

Third, the system does not permit blood separation and storage without removal of white blood cells even in the case where it is not necessary to remove white blood cells to make collected blood into blood products for blood transfusion.

Fourth, the system needs moist heat sterilization (in an autoclave) because the bag contains anticoagulant, blood preservative, etc. This moist heat sterilization could deteriorate the filter medium of the in-line filter connected to the bag, thereby decreasing the efficiency of leukocyte removal, in the case where the material used for filtration is not resistant to moist heat sterilization.

In order to overcome the above-mentioned disadvantages, there has been proposed a new system in which a filter and recovered bag (a recovered bag with a filter) is separated from the blood bag system. In this new system, a collected blood bag of the blood bag system is connected to the recovered bag with a filter by a connector when removal of white blood cells is required. (See Patent Document 2 below.)

However, the system proposed in Patent Document 2 needs two code numbers for one donor because the tube carried different segment numbers for the blood bag system and the recovered blood bag with the filter. This results in complicated management.

Patent Document 1:

Japanese Patent Publication No. 6-59304.

Patent Document 2:

Japanese Patent No. 2,952,433

DISCLOSURE OF THE INVENTION

It is an object of the present invention to provide a blood treatment circuit-assembling method and a filter unit, the blood treatment circuit giving most desirable products by connection with the filter unit only when removal of specific components from blood is necessary.

It is another object of the present invention to provide a blood treatment circuit-assembling method and a filter unit, the blood treatment circuit permitting the filter unit to be sterilized separately from a set of connected bags in different manners and under different conditions.

It is a further object of the present invention to provide a blood treatment circuit-assembling method and a filter unit, the blood treatment circuit permitting the aseptic connection of tubes in an easy, rapid, and adequate way.

The present invention to achieve the above-mentioned object is directed to a method for assembling a blood treatment circuit by aseptically connecting a connected bag set, which has previously been sterilized, and a filter unit, which has previously been sterilized, to each other, the connected bag set being composed of a primary bag holding collected blood and a secondary bag holding blood or blood components and a first tube to connect the primary bag to the secondary bag, the filter unit having an inlet and outlet, a filter medium to remove specific components from a fluid introduced through the inlet, and a second tube both ends of which are connected to the inlet and outlet, wherein the method includes a step of aseptically connecting the first tube to the second tube by using an apparatus for aseptically connecting tubes, thereby placing the filter unit along the first tube.

Thus, according to the present invention, blood treatment is performed by connecting the filter unit only when it is necessary to remove specific components from blood. This makes it possible to obtain suitable products depending on the situations such as individual patients and cases. Moreover, the method of the present invention permits easy, rapid, and accurate operation (including tube connection).

The present invention is also directed to a method for assembling a blood treatment circuit, the method including a step of sterilizing a connected bag set which is composed of a primary bag holding collected blood and a secondary bag holding blood or blood components and a first tube to connect the primary bag to the secondary bag, a step of sterilizing a filter unit having an inlet and outlet, a filter medium to remove specific components from a fluid introduced through the inlet, and a second tube both ends of which are connected to the inlet and outlet, and a step of aseptically connecting the first tube to the second tube by using an apparatus for aseptically connecting tubes, thereby placing the filter unit along the first tube.

The foregoing method not only produces the same effect as mentioned above but also makes it possible to sterilize the connected bag set and the filter separately by the most suitable method under the most suitable condition. Sterilization in such a manner preserves the performance of the filter medium and ensures a high rate of removal of specific components.

The present invention is directed also to a method for assembling a blood treatment circuit by aseptically connecting a connected bag set, which has previously sterilized, and a filter unit, which has previously sterilized, to each other, the connected bag set being composed of a primary bag holding collected blood and a plurality of secondary bags holding blood or blood components and a first tube to connect the primary bag to the secondary bags and a third tube to connect the secondary bags to one another, the filter unit having an inlet and outlet, a filter medium to remove specific components from a fluid introduced through the inlet, and a second tube both ends of which are connected to the inlet and outlet, wherein the method includes a step of aseptically connecting the third tube to the second tube by using an apparatus for aseptically connecting tubes, thereby placing the filter unit along the third tube.

Thus, according to the present invention, blood treatment is performed by connecting the filter unit only when it is necessary to remove specific components from blood. This is makes it possible to obtain suitable products depending on the situations such as individual patients and cases. Moreover, the method of the present invention permits easy, rapid, and accurate operation (including tube connection).

The present invention is also directed to a method for assembling a blood treatment circuit, the method including a step of sterilizing a connected bag set which is composed of a primary bag holding collected blood and a plurality of secondary bags holding blood or blood components, a first tube to connect the primary bag to the secondary bags, and a third tube that connects the secondary bags to one another, a step of sterilizing a filter unit having an inlet and outlet, a filter medium to remove specific components from a fluid introduced through the inlet, and a second tube both ends of which are connected to the inlet and outlet, and a step of aseptically connecting the third tube to the second tube by using an apparatus for aseptically connecting tubes, thereby placing the filter unit along the third tube.

The foregoing method not only produces the same effect as mentioned above but also makes it possible to sterilize the connected bag set and the filter separately by the most suitable method under the most suitable condition. Sterilization in such a manner preserves the performance of the filter medium and ensures a high rate of removal of specific components.

The present invention is also directed to a filter unit which includes an inlet and outlet, a filter medium to remove specific components from fluid introduced through the inlet, and a tube both ends of which are connected to the inlet and the outlet, the filter unit being put to use by cutting the tube midway and aseptically connecting the cut tubes to another tube.

Thus, according to the present invention, blood treatment is performed by connecting the filter unit only when it is necessary to remove specific components from blood. This makes it possible to obtain suitable products depending on the situations such as individual patients and cases. Moreover, the method of the present invention permits easy, rapid, and accurate operation (including tube connection).

The present invention is also directed to a filter unit to be used in the method for assembling a blood treatment circuit as mentioned above, which includes an inlet and outlet, a filter medium to remove specific components from fluid introduced through the inlet, and a tube both ends of which are connected to the inlet and outlet.

Thus, according to the present invention, the filter unit is connected only when it is necessary to remove specific components from blood. This makes it possible to obtain suitable products depending on the situations such as individual patients and cases. Moreover, the method of the present invention permits easy, rapid, and accurate operation (including tube connection).

According to the present invention, the method for assembling a blood treatment circuit should preferably be modified such that the first tube and/or the second tube has a mark that indicates the position to be connected.

According to the present invention, the method for assembling a blood treatment circuit should preferably be modified such that the second tube and/or the third tube has a mark that indicates the position to be connected.

The marks should preferably be ones which indicate the direction of flow of fluid in the tube.

According to the present invention, the method for assembling a blood treatment circuit should preferably be modified such that the tubes have additional marks that permit one to confirm that the tubes have been correctly connected to each other.

The additional marks should preferably be ones which are formed by expanding the outside diameter of the tube.

According to the present invention, the method for assembling a blood treatment circuit should preferably be modified such that the connected bag set and the filter unit are sterilized in different manners or under different conditions.

In this case, the connected bag set should preferably be sterilized by moist heat sterilization and the filter unit should preferably be sterilized by gas sterilization or radiation sterilization. Sterilization in this manner preserves the performance of the filter medium and keeps high the rate of removal of specific components.

According to the present invention, the filter unit should preferably be modified such that the tube has a mark that indicates the position to be connected to another tube.

The mark should preferably be one which indicates the direction of flow of fluid in the tube.

According to the present invention, the filter unit should preferably be modified such that the tube has an additional mark that permits one to confirm that the tube has been correctly connected to another tube.

The additional mark should preferably be one which is formed by expanding the outside diameter of the tube.

In the filter unit according to the present invention, the other tube is a tube that connects the primary bag holding collected blood to the secondary bag holding blood or blood components.

In the filter unit according to the present invention, the other tube is a tube that connects a plurality of secondary bags to each other, the secondary bags holding blood or blood components.

The filter unit according to the present invention should preferably have an additional mark that permits one to confirm that the tubes have been correctly connected to each other.

The filter unit according to the present invention should preferably be sterilized differently (in terms of method or condition) from the connected bag set.

The filter unit according to the present invention should preferably be one which is sterilized by gas sterilization or radiation sterilization. Sterilization in this manner preserves the performance of the filter medium and keeps high the rate of removal of specific components.

According to the present invention, the method for assembling the blood treatment circuit should preferably employ an aseptic tube connecting apparatus of rotary type. This apparatus needs only one step for connection of the cut ends of two tubes to be connected to each other. Therefore, it permits easy, rapid, and sure connection of tubes, without wasting tubes.

According to the present invention, the blood treatment circuit assembling method and the filter unit should preferably employ a leukocyte-removing filter as the filter.

According to the present invention, the blood treatment circuit assembling method and the filter unit should preferably have a by-pass tube that goes around the filter.

BEST MODE FOR CARRYING OUT THE INVENTION

The following is a detailed description about the embodiments of the present invention which cover the blood treatment circuit assembling method and the filter unit as illustrated in the accompanying drawings.

1. The First Embodiment

Figure 1:
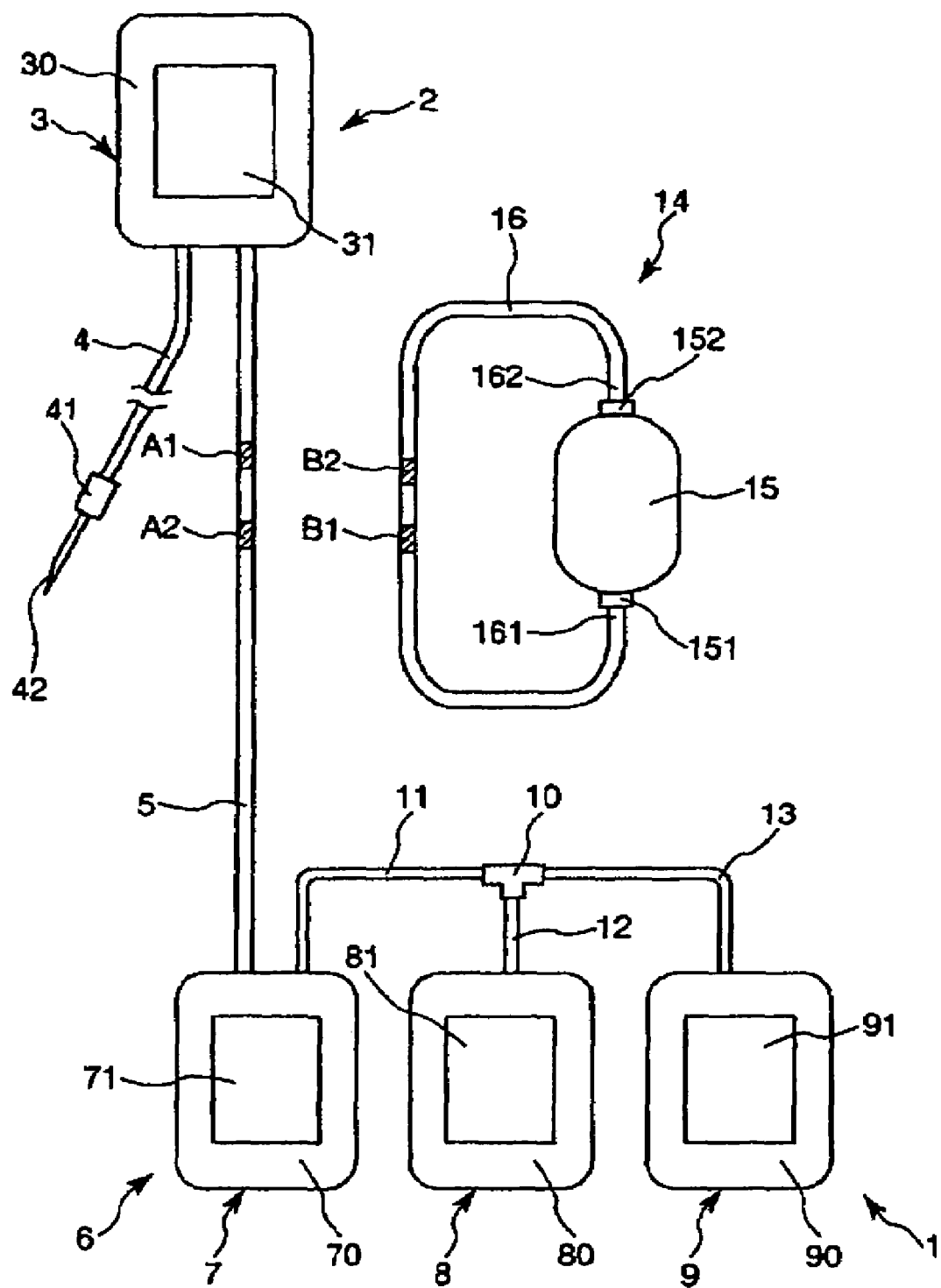
FIG. 1 is a schematic plan view showing a filter unit and a method for assembling a blood treatment circuit incorporated with the filter unit in the first embodiment of the present invention.
Figure 2:
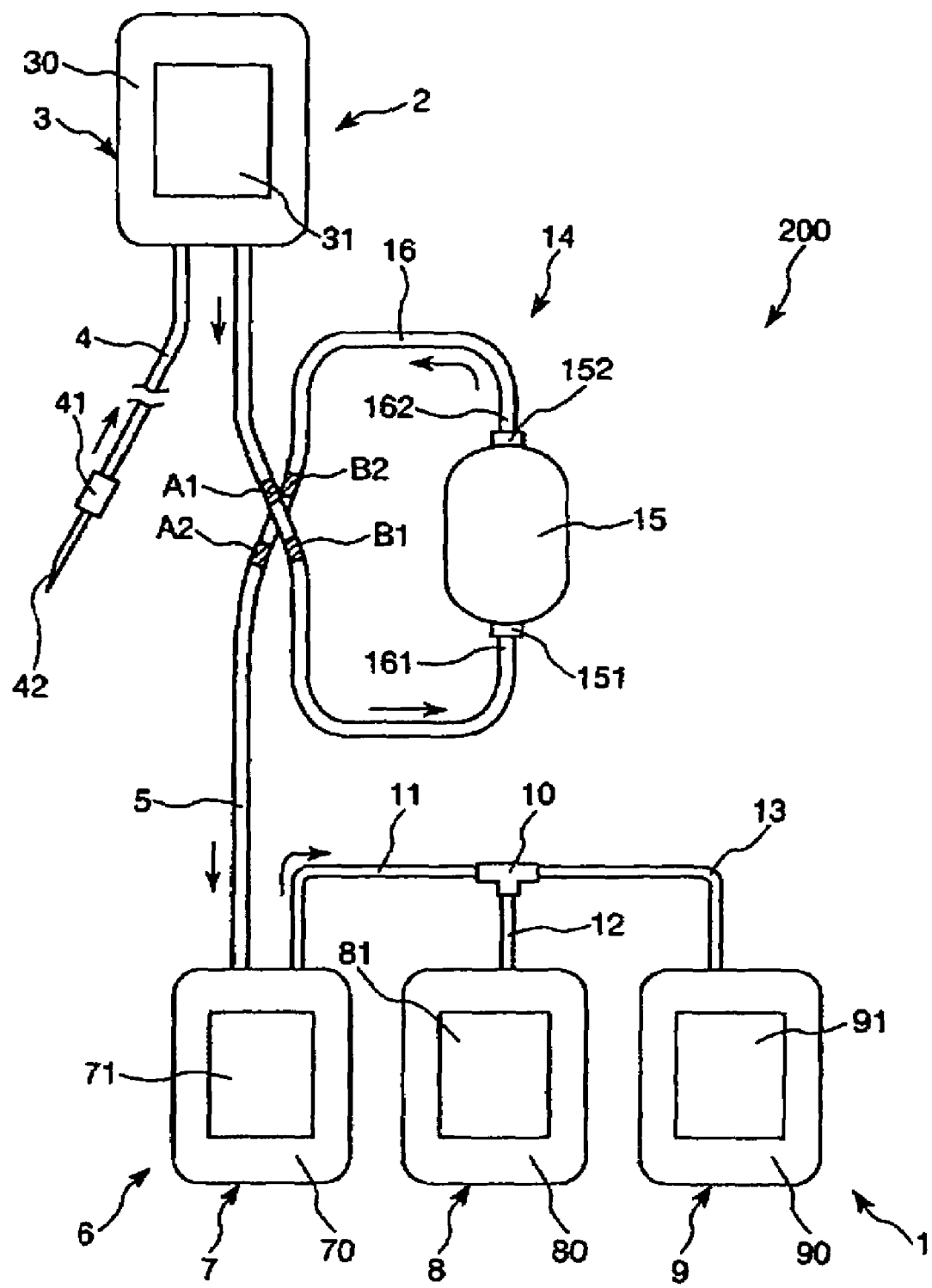
FIG. 2 is a schematic plan view showing a blood treatment circuit assembled by the method for assembling a blood treatment circuit according to the first embodiment of the present invention.

FIG. 1 is a schematic plan view showing a filter unit and a method for assembling a blood treatment circuit incorporated with the filter unit in the first embodiment of the present invention. FIG. 2 is a schematic plan view showing a blood treatment circuit assembled by the method for assembling a blood treatment circuit according to the first embodiment of the present invention.

According to the method of the present invention, the blood treatment circuit 200 is assembled by aseptically connecting the tube of the filter unit 14 to the tube of the connected bag set (blood treatment set) 1, so that the filter unit 14 is incorporated into the connected bag set 1 and the blood treatment circuit 200 is obtained as desired.

The connected bag set 1 and the filter unit 14 are constructed as follows.

The connected bag set 1 has the blood collecting part 2 and the blood treatment part 6, which are connected to each other by the first tube 5 before use.

The blood collecting part 2 has the primary bag 3 (which stores collected blood), the blood collecting tube 4 (which introduces blood into the primary bag 3), and the first tube 5 (which discharges blood from the primary bag 3).

The primary bag 3 has the bag proper 30 which is formed of laminated flexible sheets, with their periphery heat-sealed. Incidentally, the bag proper 30 of the primary bag 3 may have any structure; for example, a tubular sheet, with its open ends heat-sealed, from a folded flat sheet, with its three open sides heat-sealed, etc.

The bag proper 30 may be made of any material selected from polyvinyl chloride, flexible polyvinyl chloride (and its copolymer, polymer blend, or polymer alloy with other polymer in small quantity), and ethylene-vinyl acetate copolymer.

It is desirable that the primary bag 3 previously contains an anticoagulant. This anticoagulant is usually a liquid, such as ACD-A solution, CPD solution, CPDA-1 solution, and heparin sodium solution. Its amount in the bag proper 30 varies depending on the amount of blood to be collected.

As shown in FIG. 1, to the lower side of the primary bag 3 are connected one end of the flexible tube 4 and one end of the (first) tube 5 for communication with the inside of the primary bag 3 where blood is held.

The flexible tube 4 introduces collected blood to the primary bag 3. The first tube 5 transfers blood from the primary bag 3 to the filter 15 (mentioned later).

The other end of the tube 4 is provided with the blood collecting needle 42 through the hub 41, which has a cap (not shown) that covers the blood collecting needle 42.

The tube 5 is to be connected to the tube 16 of the filter unit 14 (mentioned later). It has marks A1 and A2 at specific positions on its surface, as shown in FIG. 1. These marks indicate the position for connection to ensure tube connection at adequate positions.

The marks A1 and A2 may be formed in any manner; for example, by coloring, by printing with letters, figures, or symbols, by surface roughening, by expanding or contracting the tube diameter, or by deforming the tube (such as curving, bending, flattening, and branching). These means may be used in combination with one another. The shape and number of the marks A1 and A2 are not specifically restricted.

There are no restrictions in the method of forming the marks A1 and A2. Conceivable methods include ink printing, laser printing, stamping, transcription, surface roughening (or embossing), heat or pressure molding, sticking of label or tape, attaching of ring, band, or belt, modifying of the tube material or color, or connecting another material to the tube.

When the blood treatment circuit 200 has been finally completed (or the filter unit 14 has been incorporated into the blood treatment circuit 200), the mark A1 is at the up-stream side in the blood treatment circuit and the mark A2 is at the down-stream side (see FIG. 2). The marks A1 and A2 should preferably differ in color, shape, size, symbol, etc. (taking color as an example hereinafter) so that they can be distinguished from each other easily. In this way it is possible to ensure the correct connection of the tube 5 and the tube 16.

The blood treatment part 6 separates blood into several blood components and recovers desired blood components only. It has tube-connected three secondary bags 7, 8, and 9, which hold the recovered blood components.

According to this embodiment, the secondary bag 7 functions as the red blood cell bag that holds concentrated red blood cell (CRC), the secondary bag 8 functions as the platelet bag that holds platelet concentrated (PC), and the secondary bag 9 functions as the plasma bag that holds platelet-poor plasma (PPP).

The secondary bags 7, 8, and 9 respectively have the bag propers 70, 80, and 90, which are formed of laminated flexible sheets, with their periphery heat-sealed. They are not specifically restricted in their shape. As in the case of the bag proper 30 mentioned above, they may be a tubular sheet, with its open ends heat-sealed, or from a folded sheet, with its three open sides heat-sealed.

The bag propers 70, 80, and 90 may be made of any material selected from polyvinyl chloride, flexible polyvinyl chloride (and its copolymer, polymer blend, or polymer alloy with other polymer in small quantity), and ethylene-vinyl acetate copolymer.

It is desirable that the secondary bag 9 (or the bag proper 70) previously contains an erythrocyte preserving solution, which is usually a liquid, such as SAGM solution, OPTISOL solution, and MAP solution. Its amount in the bag proper 90 varies depending on the amount of blood to be collected.

As shown in FIG. 1, to the upper side of the secondary bag 7 are connected the other end of the tube 5 and one end of the third tube 11 for communication with the inside of the secondary bag 7 where blood is held. The tube 5 introduces blood (or blood component) to the secondary bag 7. The tube 11 transfers blood from the secondary bag 7 to the secondary bag 8.

As shown in FIG. 1, to the upper side of the secondary bag 8 is connected one end of the flexible third tube 12 for communication with the inside of the secondary bag 8 where blood component is held. To the upper side of the secondary bag 9 is connected one end of the third tube 13 for communication with the inside of the secondary bag 9 where blood component is held. The opposite ends of the tubes 11, 12, and 13 are connected respectively to the three ports of the three-way branching connector 10 (T-tube, Y-tube, or three-way cock).

In this way the secondary bags 7, 8, and 9 are connected to one another through the tubes 11, 12, and 13 and the branching connector 10, so that they communicate with one another.

The tubes 4, 5, 11, 12, and 13 and the tube 16 (mentioned later) may be made of any material selected from polyvinyl chloride, flexible polyvinyl chloride (and its copolymer, polymer blend, or polymer alloy with other polymer in small quantity), and ethylene-vinyl acetate copolymer.

Each bag proper 30, 70, 80, and 90 has a label 31, 71, 81, and 91 stuck thereto. Each of the labels 31, 71, 81 and 91 has an adhesive layer on its rear surface and adheres to each of the bag propers 30, 70, 80 and 90, respectively, via the adhesive layer.

These labels 31, 71, 81, and 91 carry information (printed thereon) about the content of the bag. Such information includes kind of blood component, capacity of bag, blood group, date of blood collection, and donor's name, age, and sex. It may be expressed by means of letters, numerals, symbols, or codes (bar code or two-dimensional code).

The labels 31, 71, 81, and 91 should preferably have not only good adherence to each bag proper 30, 70, 80, and 90 but also good moisture resistance.

The connected bag set 1 mentioned above is previously sterilized, preferably by moist heat sterilization (in an autoclave) because each bag contains anticoagulant, blood preservative, etc. as mentioned above.

As shown in FIG. 1, the filter unit 14 includes the filter 15 (which has the inlet 151 and the outlet 152) and the second tube 16 (to both ends of which are connected the inlet 151 and the outlet 152).

The filter 15 is included of a housing and a filter medium placed therein. It receives blood from the inlet 151 and discharges desired components (unnecessary components) from the outlet 152 after filtration by the filter medium.

The housing of the filter 15 may be made of any material selected from polycarbonate, polyvinyl chloride, flexible polyvinyl chloride, ethylene-vinyl acetate copolymer, acrylonitrile-butadiene-styrene copolymer (ABS resin), and acrylonitrile-styrene copolymer (AS resin).

The filter medium in the filter 15 may be made of porous material or nonwoven fabric of polyether polyurethane, polyester polyurethane, polyethylene terephthalate, or polybutylene terephthalate.

The filter 15 is not specifically restricted in its type. It is selected according to its use. It may be classified as follows according to the components to be filtered out. Leukocyte removing filter, platelet removing filter, erythrocyte removing filter, microaggregate removing filter, virus removing filter, and endotoxin removing filter. Other filters include those which are designed to remove microbes (including bacteria), proteins (including prion, enzyme, cytokine, etc.), ions, pathogenic substances, and any foreign matter. The filter may have two or more of the above-mentioned functions.

The leukocyte removing filter may be classified into two types: one designed to separate leukocyte only (or to separate one or more than one of lymph cells, granular leukocyte, and monocyte); and one designed to separate leukocyte and platelet. It may also be designed to separate microaggregate together with leukocyte.

The microaggregate removing filter may be classified into two types: one designed to remove microaggregate only; and one designed to remove microaggregate and platelet.

The virus removing filter may be classified into two types: one designed to remove virus only (such as HAV, HBV, HCV, HIV, HTLV-1, CMV, parvovirus B19, filovirus, and hantavirus); and one designed to remove virus together with either or both of endotoxin and microaggregate. It may also be designed to selectively remove leukocyte and platelet.

The endotoxin removing filter may be classified into two types: one designed to remove endotoxin only; and one designed to remove either or both of virus and microaggregate. It may also be designed to selectively remove leukocyte and platelet.

Incidentally, in the following description, the filter 15 is typified by a leukocyte removing filter that separates (filters out) leukocyte from blood.

The second tube 16 shown in FIG. 1 is a single continuous tube, with its end 161 connected to the inlet 151 and its end 162 connected to the outlet 152. Thus the filter unit 14 before use constitutes a closed cyclic circuit with the tube 16 and the filter 15.

The tube 16 is to be connected to the tube 5 of the connected bag set 1. It has marks B1 and B2 at specific positions on its surface, as shown in FIG. 1. These marks indicate the positions to be connected to ensure tube connection at adequate positions.

The marks B1 and B2 may be formed in any manner; for example, by coloring, by printing with letters, figures, or symbols, by surface roughening, by expanding or contracting the tube diameter, or by deforming the tube (such as curving, bending, flattening, and branching). These means may be used in combination with one another. The shape and number of the marks B1 and B2 are not specifically restricted.

There are no restrictions in the method of forming the marks B1 and B2. Conceivable methods include ink printing, laser printing, stamping, transcription, surface roughening (or embossing), heat or pressure molding, sticking of label or tape, attaching of ring, band, or belt, modifying of the tube material or color, or connecting another material to the tube.

When the blood treatment circuit 200 has been finally completed (or the filter unit 14 has been incorporated into the connected bag set 1), the mark B1 is at the up-steam side in the blood treatment circuit 200 and the mark B2 is at the downstream side (see FIG. 2). The marks B1 and B2 should preferably differ in color, shape, size, symbol, etc. (taking color as an example hereinafter) so that they can be distinguished easily from each other. In this way it is possible to ensure the correct connection of the tube 5 and the tube 16.

For connection of the tube 5 to the tube 16, the tube 5 is cut between the marks A1 and A2 and the tube 16 is cut between the marks B1 and B2. Then, the cut end (close to the mark A1) of the tube 5 is connected to the cut end (close to the mark B1) of the tube 16, and the cut end (close to the mark A2) of the tube 5 is connected to the cut end (close to the mark B2) of the tube 16. See FIGS. 1 and 2.

Therefore, it is desirable that the marks A1 and B2 have the same color and the marks A2 and B1 have the same color (with A1 and A2 having different colors). This ensures connection at a right position and in a right direction.

The housing of the filter 15 should preferably have a mark (such as arrow) that indicates the direction of flow (filtration) so that the direction of connection is confirmed after the tube 5 has been connected to the tube 16.

The filter unit 14 should previously been sterilized. (Sterilization of the filter unit 14 should preferably be performed differently from that of the connected bag set 1.) Preferred methods for sterilization of the filter unit 14 include gas sterilization (with ethylene oxide gas) and radiation sterilization (with γ rays). These sterilizing methods are less harmful to the filter medium of the filter 15 than moist heat sterilization. Thus the sterilized filter medium fully produces its effect and effectively removes white blood cells.

In the present invention, the connected bag set 1 and the filter unit 14 may be sterilized in the same way or under different conditions suitable for them. For example, moist heat sterilization for the connected bag set 1 may be carried out under conditions (duration and temperature) suitable for the anticoagulant and erythrocyte preservative, and moist heat sterilization for the filter unit 14 may be carried out under different conditions (duration and temperature) for complete sterilization without adverse effect on the filtering performance. In this way it is possible to permit the filter unit 14 to remove white blood cells efficiently.

The connected bag set 1 and the filter unit 14, which have been sterilized as mentioned above, are subsequently assembled into the blood treatment circuit 200 by aseptically connecting the tube 5 with the tube 16 at their specified positions. Connection is accomplished by using an apparatus for aseptic connection of tubes (not shown). The method for assembling the blood treatment circuit according to the present invention will be described in more detail in the following.

[1] Sterilization of the Connected Bag Set

The first step is sterilization of the connected bag set 1. Moist heat sterilization (in an autoclave) is preferable.

[2] Sterilization of the Filter Unit

The second step is sterilization of the filter unit 14. Gas sterilization (with ethylene oxide) or radiation sterilization (with γ rays) is preferable. Sterilization in this manner is less liable to deteriorate the performance of the filter medium.

Incidentally, the filter unit 14 and the connected bag set 1 may be sterilized in the same way (for example, moist heat sterilization). In this case, adequate sterilizing conditions should be selected so that the filter medium fully exhibits its performance.

[3] Incorporation of the Filter Unit Into the Connected Bag Set

The tube 5 is connected to the tube 16 at their specific positions by using an apparatus for aseptic connection of tubes (not shown). The position and direction for connection of the tube 5 and the tube 16 should conform to the marks A1, A2, B1, and B2 mentioned above. In this way the tubes 5 and 16 can be connected to the apparatus for aseptic connection easily and adequately without mistakes.

The apparatus for aseptic connection of tubes may be selected from any known ones. Those of rotary type are preferable which is disclosed in Japanese Patent Laid-Open Publication Nos. 9-154920 and 2000-308688.

The disclosed apparatus has two tube holders which hold two tubes (the tubes 5 and 16) arranged parallel to each other at two positions with a certain distance apart in the lengthwise direction. It also has a heat cutting blade which advances and retracts between the tube holders. The heat cutting blade (wafer) cuts the two tubes all at once by melting. Then, one of the tube holders is turned about 180° with respect to the other, so that one tube is connected to the other at their cut surfaces. In other words, melt cutting is performed on the tube 5 at a position between the marks A1 and A2 and on the tube 16 at a position between the marks B1 and B2. The cut end close to the mark A1 of the tube 5 is connected to the cut end close to the mark B1 of the tube 16, and the cut end close to the mark A2 of the tube 5 is connected to the cut end close to the mark B2 of the tube 16. See FIGS. 1 and 2.

The aseptic tube connecting apparatus of rotary type mentioned above needs only one step for connection of the cut end close to the mark A1 of the tube 5 with the cut end close to the mark B1 of the tube 16, and connection of the cut end close to the mark A2 of the tube 5 with the cut end close to the mark B2 of the tube 16. Therefore, it permits easy, rapid, and sure connection of tubes, without wasting tubes.

Aseptic connection of the tubes 5 and 16, which is performed as mentioned above, completes incorporation of the filter unit 14 into the connected bag set 1. Now the blood treatment circuit 200 is finished.

Connection of the tubes 5 and 16 should preferably be accomplished such that the length of flow path from the lower side of the primary bag 3 of the tube 5 to the inlet 151 of the filter 15 is constant. See FIG. 2. The constant length of flow path ensures a constant flow rate for the filter 15, which leads to uniform and maximum filtering performance when blood is discharged from the primary bag 3 and transferred by its own weight. As a result, the filter 15 removes white blood cells uniformly and efficiently, which improves the quality of the final blood products (blood components such as erythrocyte, platelet, and plasma). In addition, the marks A1, A1, B1, and B2 help connect the tubes 5 and 16 easily and surely at adequate positions while keeping constant the length of flow path as mentioned above.

The blood treatment circuit 200 assembled as mentioned above is used in the following manner. Incidentally, it is assumed that the filter 15 is typically a leukocyte removing filter.

[1A] The first step is to collect blood from a donor by sticking the blood collecting needle 42 of blood collecting part 2 into the donor's vessel, so that a prescribed amount of collected blood is stored in the primary bag 3. At this time, the tube 5 should preferably be sealed with a breakable stopper or the like to prevent blood from flowing from the primary bag 3 to the tube 5.

After blood collection is completed, a portion along the tube 4 is sealed by fusion bonding with a tube sealer or the like, if necessary, and the sealed part is cut to separate and remove the part of the tube 4 which is connected to the blood collecting needle 42.

[2A] In the second step, the seal of the tube 5 with the breakable stopper or the like is released, so that the blood in the primary bag 3 is discharged through the tube 5 and passed through the filter 15 for separation of white blood cells from the blood. To facilitate this procedure, the primary bag 3 holding blood is suspended high from a stand or the like so that blood flows by gravity.

The blood discharged from the primary bag 3 flows through the tubes 5 and 16 in the direction of arrow (shown in FIG. 2) and enters the filter 15 from the inlet 151. In the filter 15, white blood cells are removed (filtered off) by the filter medium. The blood, from which white blood cells have been removed, is discharged from the outlet 152 and introduced into the secondary bag 7 through the tubes 16 and 5.

As mentioned above, the tubes 5 and 16 are connected to each other such that the length of flow path from the lower side of the primary bag 3 to which the tube 5 is connected, to the inlet 151 of the filter 15 is constant. See FIG. 2. This construction keeps constant the rate of filtration through the filter 15 and permits the filter 15 to fully and uniformly exhibit its performance. Thus the filter 15 removes white blood cells uniformly and efficiently, thereby improving the quality of blood products (blood components such as erythrocyte, platelet, and plasma).

[3A] After leukocyte-free blood has been recovered in the secondary bag 7, the tube 5 is sealed at a position near the secondary bag 7 by using a tube sealer or the like. Then the sealed part is cut to separate the blood treatment part 6 from the blood collecting part 2 and the filter unit 14.

[4A] The secondary bags 7, 8, and 9 of the blood treatment part 6 are placed all together in the cup of the centrifuge and the leukocyte-free blood is centrifuged. As the result of centrifugation, for example, the leukocyte-free blood in the secondary bag 7 separates into two layers, the lower layer containing erythrocytes and the upper layer containing platelet rich plasma. The pattern of separation of blood components depends on the conditions of centrifugation (such as revolution and duration).

[5A] Then, the upper layer (containing platelet rich plasma) in the secondary bag 7 is transferred to the secondary bag 8 in the following manner.

The secondary bag 7 is set on a bag pressing apparatus to separate and transfer blood components. With the tube 13 sealed with a clamp, the secondary bag 7 is gradually pressed, so that the supernatant platelet rich plasma is discharged from the secondary bag 7 and transferred to the secondary bag 8 through the tube 11, the branching connector 10, and the tube 12. What remain in the secondary bag 7 are red blood cells.

[6A] After transfer of platelet rich plasma is completed, the clamp on the tube 13 is released. With the tube 12 sealed with a clamp, the erythrocyte preserving solution in the secondary bag 9 is transferred to the secondary bag 7 (containing erythrocytes) through the tube 13, the branching connector 10, and the tube 11.

[7A] A portion along the tube 11 is sealed by fusion bonding with a tube sealer or the like and the sealed part is cut to separate the secondary bag 7 from the secondary bags 8 and 9. The secondary bag 7 is shaken to thoroughly mix together the erythrocyte and the erythrocyte preserving solution.

Now, the secondary bag 7 contains concentrated red blood cells (CRC).

[8A] The secondary bags 8 and 9 are placed all together in the cup of the centrifuge for centrifugation.

As the result of centrifugation, the platelet rich plasma in the secondary bag 8 separates into platelet (precipitate) and platelet-poor plasma (supernatant).

The pattern of separation of blood components depends on the conditions of centrifugation.

[9A] The secondary bag 8 is set on a bag pressing apparatus (to separate and transfer blood components), and the secondary bag 8 is gradually pressed.

In this way the supernatant plasma is discharged from the secondary bag 8 and transferred to the secondary bag 9 through the tube 12, the branching connector 10, and the tube 13. This step should be carried out such that an adequate amount of plasma remains in the secondary bag 8 which is necessary to prepare platelet concentrated (platelet suspension).

[10A] Then, portions along the tubes 12 and 13 are sealed by fusion bonding (with the help of a tube sealer or the like), and the sealed part is cut to separate the secondary bag 8 and the secondary bag 9 from each other, so that platelet precipitates in the secondary bag 8 are suspended in the plasma.

Thus there are obtained the secondary bag 8, which contains platelet or platelet concentrated (PC), and the secondary bag 9, which contains plasma or platelet-poor plasma (PPP).

In this way there are obtained different kinds of blood products, or red blood cells (concentrated red blood cells (CRC)) contained in the secondary bag 7, platelets (platelet concentrated (PC)) contained in the secondary bag 8, and plasma (platelet-poor plasma (PPP)) contained in the secondary bag 9.

The above-mentioned procedure for blood separation and recovery is a mere example, and the present invention is not restricted in the kind of blood components to be separated and recovered, the number and kind of bags, and the order of steps.

2. The Second Embodiment

Figure 3:
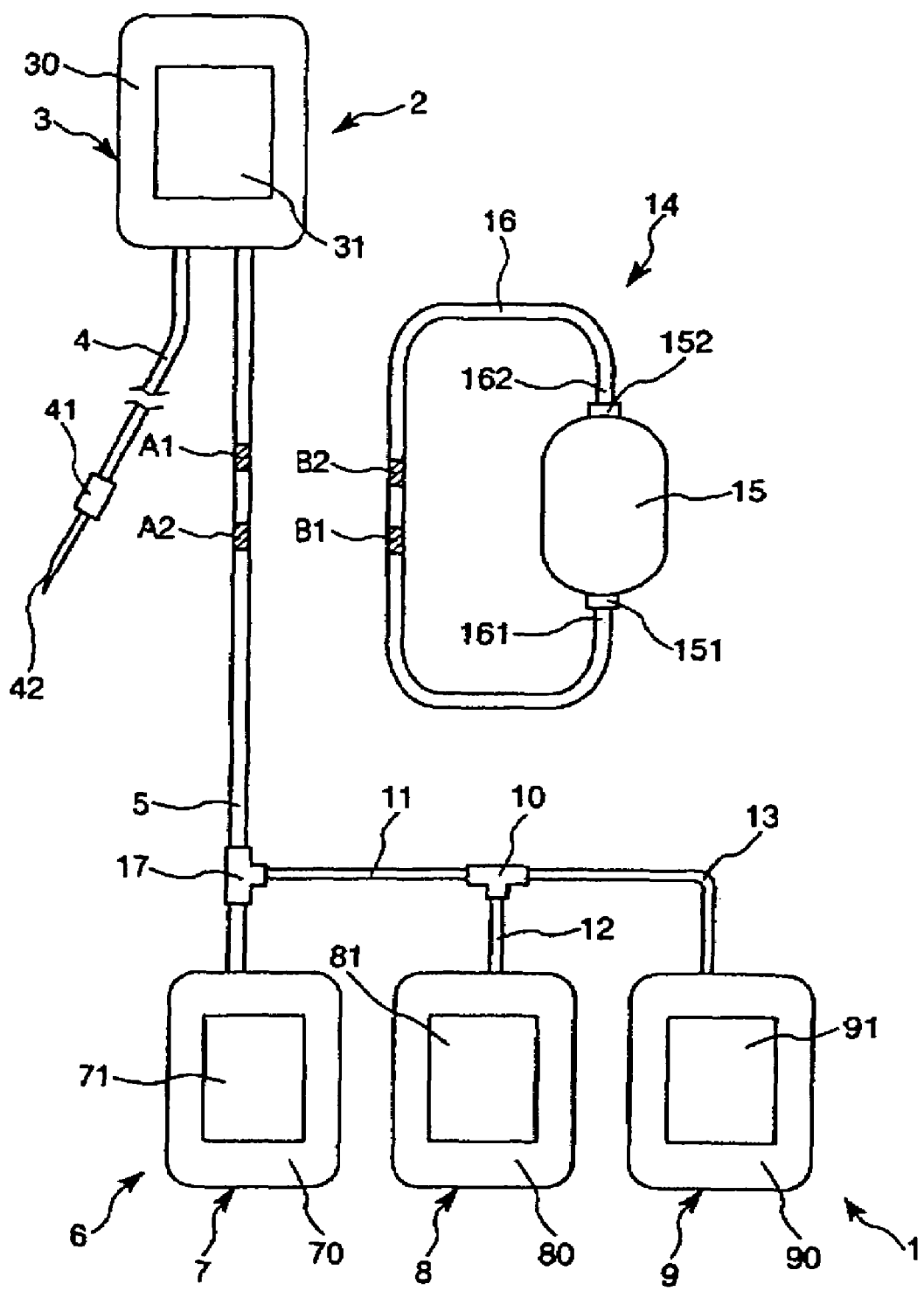
FIG. 3 is a schematic plan view showing a method for assembling a blood treatment circuit in the second embodiment of the present invention.

FIG. 3 is a schematic plan view showing a method for assembling a blood treatment circuit in the second embodiment of the present invention. The difference between the first and second embodiments is described below, with common items omitted.

The second embodiment is identical with the first embodiment except for the arrangement of the tube to connect the secondary bags 7 and 8 of the connected bag set 1.

In the first embodiment, one end of the tube 11 is connected directly to the secondary bag 7, whereas in the second embodiment, one end of the tube 11 is connected to the three-way branching connector 17 (T-tube, Y-tube, or three-way cock) which is placed along the tube 5 and one end of the tube 11 (the third tube) is connected to one port of the branching connector 17.

The second embodiment is identical with the first embodiment in the constitution of the filter unit 14 and the method of assembling the blood treatment circuit 200 (or the method of connecting the tubes 5 and 16 to each other).

3. The Third Embodiment

Figure 4:
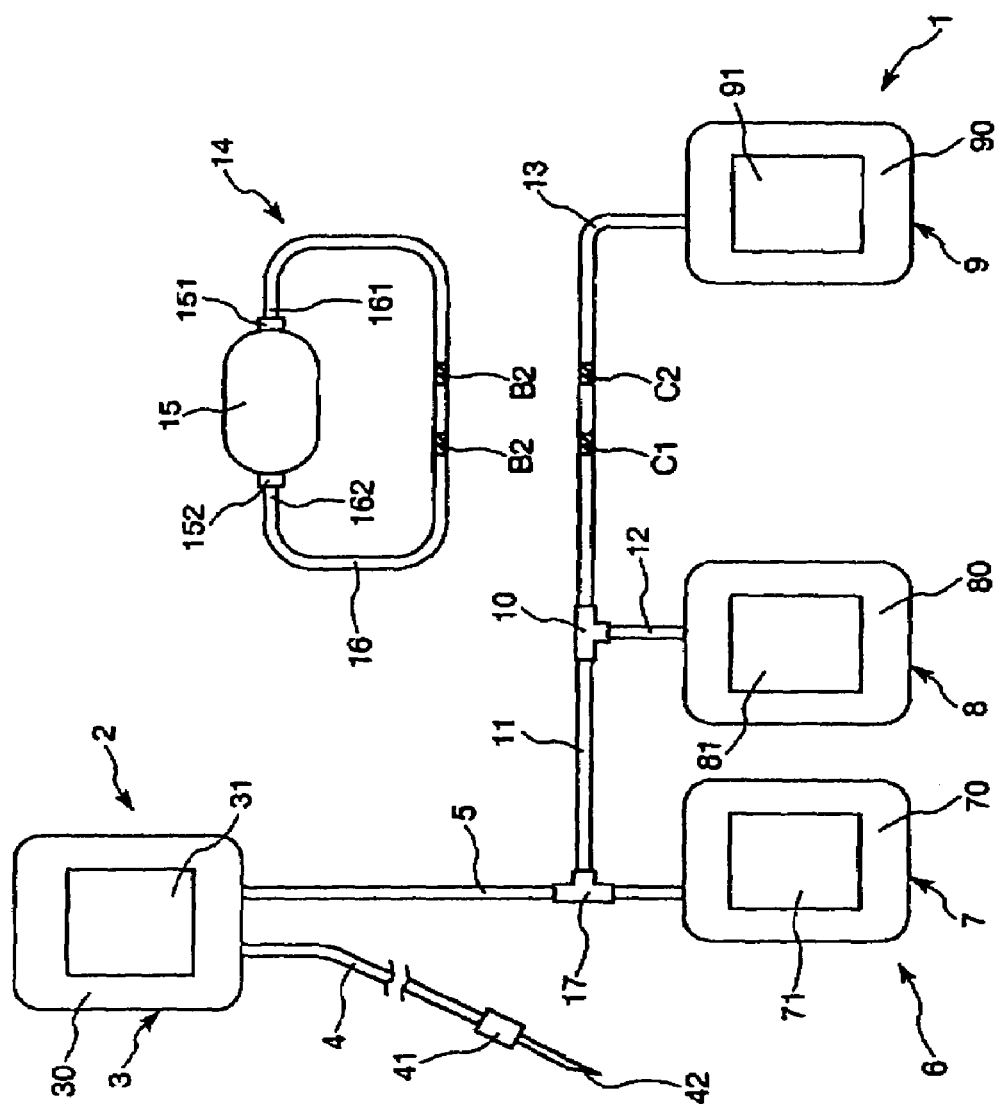
FIG. 4 is a schematic plan view showing a filter unit and a method for assembling a blood treatment circuit incorporated with the filter unit in the third embodiment of the present invention.
Figure 5:
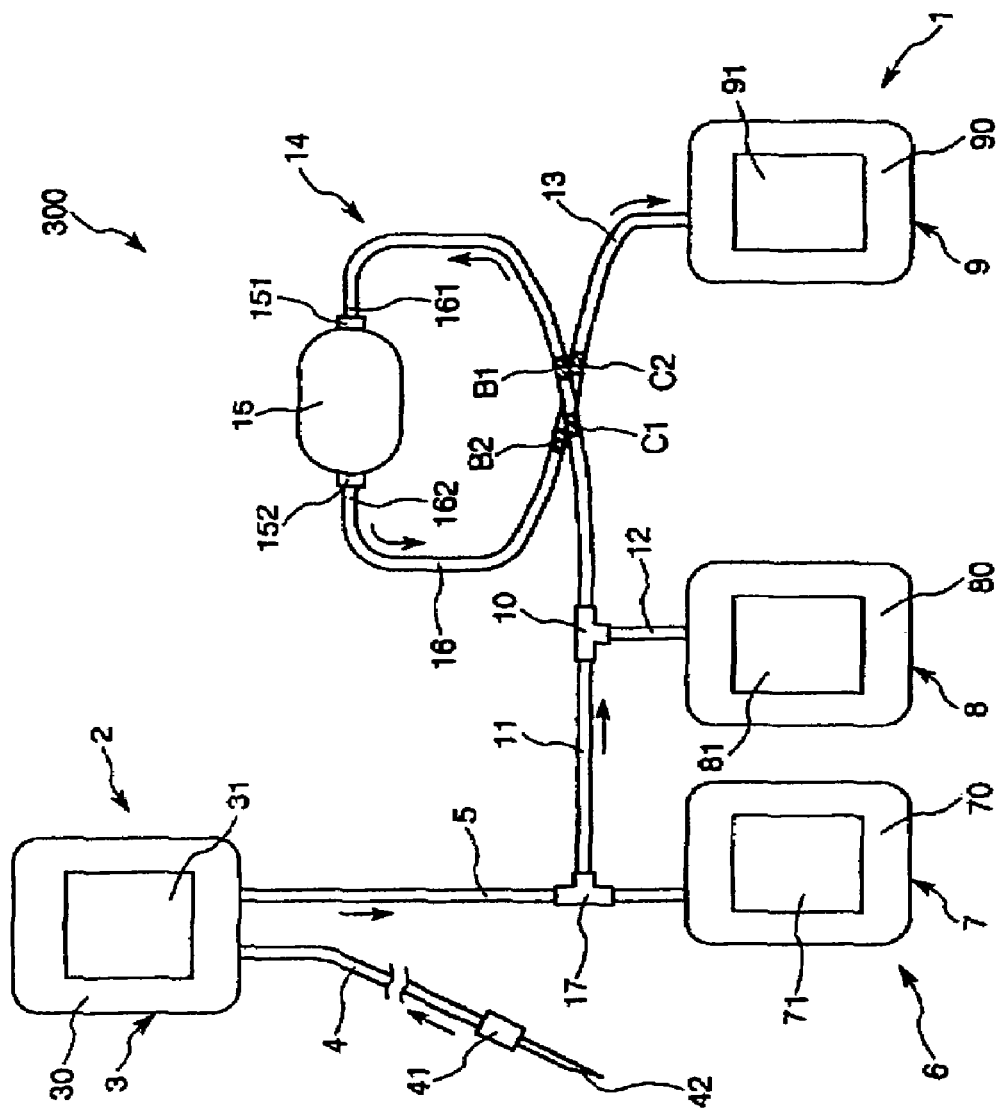
FIG. 5 is a schematic plan view showing a blood treatment circuit assembled by the method for assembling a blood treatment circuit according to the third embodiment of the present invention.

FIG. 4 is a schematic plan view showing a filter unit and a method for assembling a blood treatment circuit incorporated with the filter unit in the third embodiment of the present invention. FIG. 5 is a schematic plan view showing a blood treatment circuit assembled by the method for assembling a blood treatment circuit according to the third embodiment of the present invention. The difference between the second and third embodiments is described below, with common items omitted.

The third embodiment is identical with the second embodiment except for the position at which the filter unit 14 is connected to the connected bag set 1. (What is mentioned for the first embodiment is applied to the third embodiment.)

In the first and second embodiments, the filter unit 14 is connected to the tube 5 (the first tube) at its middle point, whereas in the third embodiment, the tube 13 (the third tube) and the tube 16 are aseptically connected to each other so that the filter unit 14 is incorporated into the tube 13 (the third tube) to assemble the blood treatment circuit 300. See FIG. 5.

The tube 13 has marks C1 and C2 at specific positions on its surface, as shown in FIG. 4. These marks indicate the position for connection to ensure tube connection at adequate positions.

The marks C1 and C2 may be formed in the same way as the marks A1 and A2.

For the same reason as mentioned above, it is desirable that the marks C1 and B2 have the same color and the marks C2 and B1 have the same color (with C1 and C2 having different colors). This ensures connection at an appropriate position and in an appropriate direction.

The housing of the filter 15 should preferably have a mark (such as an arrow) that indicates the direction of flow (filtration) so that the direction of connection is confirmed after the tube 13 has been connected to the tube 16.

Incorporation of the filter unit 14 into the connected bag set 1 is accomplished by aseptically connecting the tube 13 to the tube 16 at their specific intermediate positions with an aseptic tube connecting apparatus of rotary type mentioned above. This tube connecting apparatus offers the same advantage as mentioned above.

The position and direction of connection for the tubes 13 and 16 should conform to the marks C1, C2, B1, and B2. In this way it is possible to mount the tubes 13 and 16 on the aseptic tube connecting apparatus easily and correctly without the possibility of erratic connection.

In the third embodiment, the secondary bag 7 holds platelet poor plasma (PPP), the secondary bag 8 holds buffy coat (BC), and the secondary bag 9 holds concentrated red blood cells (CRC).

In this embodiment, the filter unit 14 is connected to the midway of the tube 13 (the third tube); however, this is not essential. The filter unit 14 may be connected to the midway of the tube 11 (the third tube) or the tube 12 (the third tube).

The connected bag set 1 and the filter unit 14 (both shown in FIG. 4) are used in the following manner. Incidentally, it is assumed that the filter 15 is typically a leukocyte removing filter.

[1B] The first step is to collect blood from a donor by sticking the blood collecting needle 42 of blood collecting part 2 into the donor's vessel, so that a prescribed amount of collected blood is stored in the primary bag 3. During blood collection is going on, the tube 5 should preferably be sealed with a breakable stopper to prevent blood from flowing out from the primary bag 3.

After blood collection is completed, a portion along the tube 4 is sealed by fusion bonding with a tube sealer or the like, if necessary, and the sealed part is cut to separate and remove the part of the tube 4 which is connected to the blood collecting needle 42.

[2B] The primary bag 3 and the secondary bags 7, 8 and 9, which hold the collected blood, are placed all together in the cup of the centrifuge to be centrifuged. As the result of centrifugation, the blood (whole blood) held in the primary bag 3 separates into three layers, the lowermost layer containing red blood cells with white blood cells, the middle layer containing buffy coat rich with white blood cells and platelets, and the uppermost layer containing platelet-poor plasma. The pattern of separation of blood components depends on the conditions of centrifugation (such as revolution and duration).

[3B] Then, platelet-poor plasma in the uppermost layer in the primary bag 3 is transferred to the secondary bag 7 and buffy coat in the middle layer in the primary bag 3 is transferred to the secondary bag 8 both in the following manner.

The primary bag 3 is set on a bag pressing apparatus to separate and transfer blood components. With the tube 11 sealed with a clamp, the primary bag 3 is gradually pressed, so that the supernatant platelet-poor plasma is discharged from the primary bag 3 and transferred to the secondary bag 7 through the tube 5. What remain in the primary bag 3 are concentrated red blood cells and buffy coat.

[4B] After transfer of platelet poor plasma to the secondary bag 7 is completed, the clamp on the tube 11 is released. The tube 12 is sealed with a clamp, and the part of the tube 5 which is between the branching connector 17 and the secondary bag 7 is sealed with a clamp. The primary bag 3 is gradually pressed, so that the buffy coat is transferred from the primary bag 3 to the secondary bag 8.

[5B] After transfer of buffy coat is completed, the part of the tube 5 which is between the branching connector 17 and the secondary bag 7 is sealed by fusion bonding and the tube 12 is also sealed by fusion bonding by a tube sealer or the like. The sealed parts are cut. Thus there are obtained the secondary bag 7 containing platelet-poor plasma (PPP) and the secondary bag 8 containing buffy coat.

[6B] The intermediate part between the marks C1 and C2 on the tube 13 is aseptically connected to the intermediate part between the marks B1 and B2 on the tube 13 by means of an aseptic tube connecting apparatus. Thus there is obtained the blood treatment circuit 300 as shown in FIG. 5. The position and direction for connection of the tube 13 and the tube 16 should conform to the marks C1, C2, B1, and B2 mentioned above.

[7B] The erythrocyte preserving solution in the secondary bag 9 is transferred to the primary bag 3, so that it is mixed with concentrated red blood cells. That is, the erythrocyte preserving solution in the secondary bag 9 is transferred to the primary bag 3 through the tube 13, one end 162 of the tube 16, the filter 15, the other end 161 of the tube 16, the branching connector 10, the tube 11, the branching connector 17, and the tube 5, so that the erythrocyte preserving solution is added to the concentrated red blood cells in the primary bag 3. They are thoroughly mixed in the primary bag 3.

[8B] The concentrated red blood cells, to which the erythrocyte preserving solution has been added, is discharged from the primary bag 3 and transferred to the secondary bag 9 through the filter 15 for separation of white blood cells from the concentrated red blood cells. To facilitate this procedure, the primary bag 3 is suspended high from a stand so that blood flows by gravity.

The concentrated solution of red blood cells, which has been discharged from the primary bag 3, flows through the tubes 5, 11, 13, and 16 in the direction of arrow shown in FIG. 5 and enters the filter 15 through the inlet 151. The filter 15 removes (filters out) white blood cells. The concentrated solution of red blood cells, from which white blood cells have been removed, is discharged from the outlet 152 and introduced into the secondary bag 9 through the tubes 16 and 13.

[9B] The tube 13 is sealed at its intermediate position (between the mark C2 and the secondary bag 9) by means of a tube sealer or the like, and the sealed part is cut. Thus there is obtained the secondary bag 9 containing red blood cells or concentrated red blood cells (CRC).

Thus, there are obtained the secondary bag 9 containing red blood cells or concentrated red blood cells (CRC), the secondary bag 7 containing plasma or platelet-poor plasma (PPP), and the secondary bag 8 containing buffy coat.

The above-mentioned procedure for blood separation and recovery is a mere example, and the present invention is not restricted in the kind of blood components to be separated and recovered, the number and kind of bags, and the order of steps.

4. The Fourth Embodiment

Figure 6:
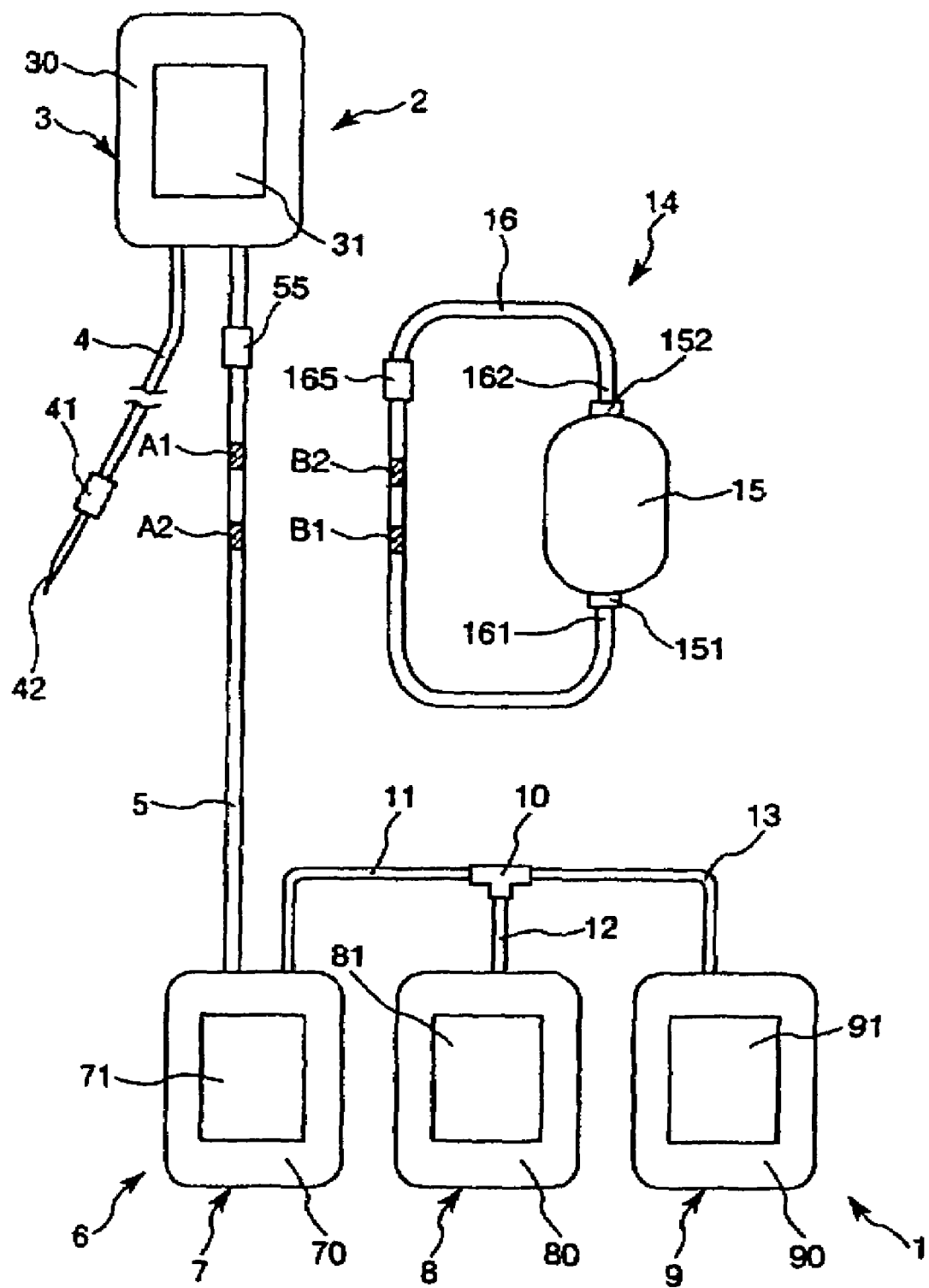
FIG. 6 is a schematic plan view showing a filter unit and a method for assembling a blood treatment circuit incorporated with the filter unit in the fourth embodiment of the present invention.
Figure 7:
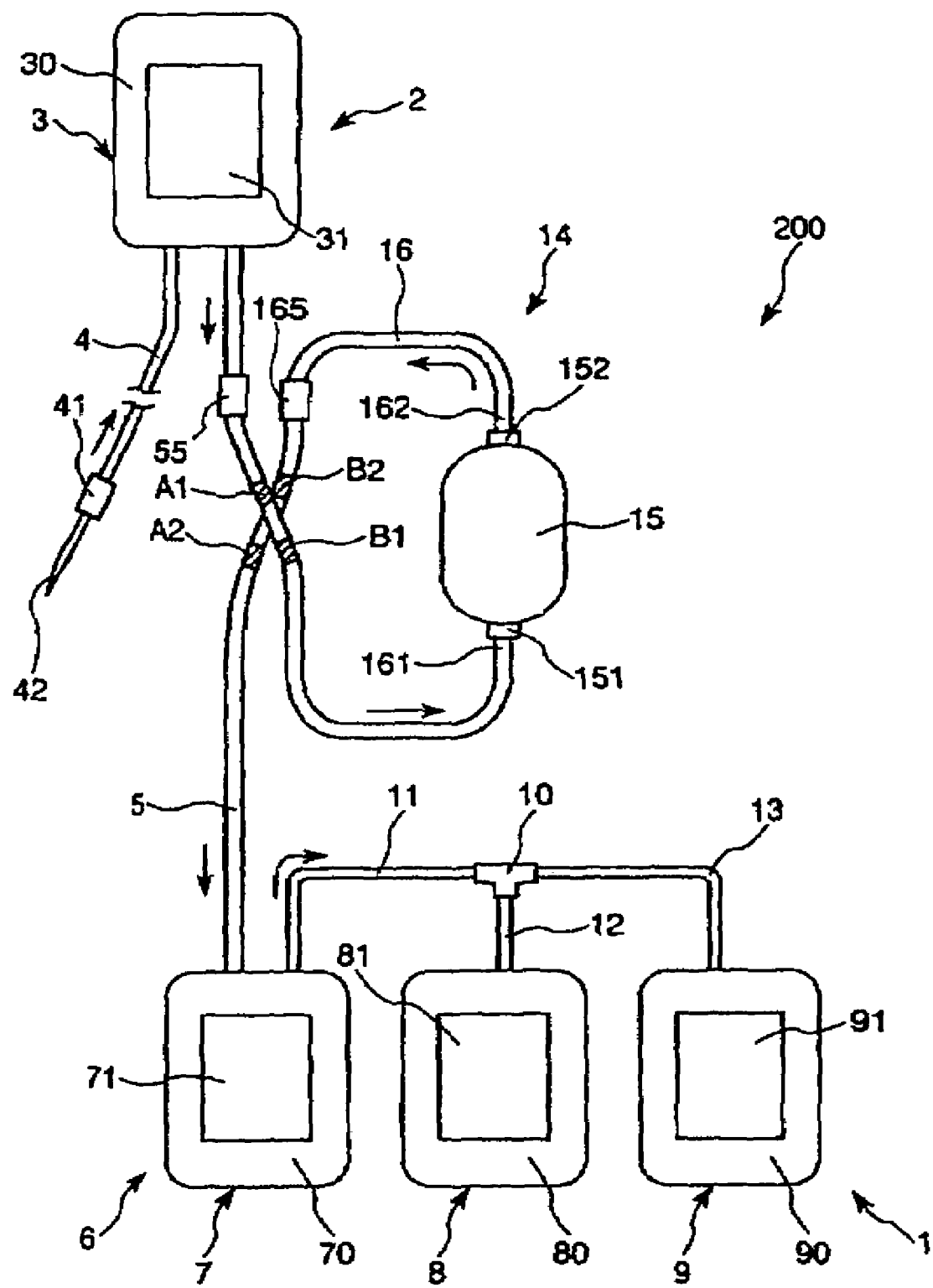
FIG. 7 is a schematic plan view showing a blood treatment circuit assembled by the method for assembling a blood treatment circuit according to the fourth embodiment of the present invention.

FIG. 6 is a schematic plan view showing a method for assembling a blood treatment circuit in the fourth embodiment of the present invention. FIG. 7 is a schematic plan view showing a blood treatment circuit assembled by the method for assembling a blood treatment circuit according to the fourth embodiment of the present invention. The difference between the first and fourth embodiments is described below, with common items omitted.

The fourth embodiment is identical with the first embodiment except that the tubes 5 and 16 have additional parts to indicate that their connection has been made correctly.

In other words, according to the fourth embodiment, the tube 5 has an expanded part 55 (which has a larger outside diameter than the tube 5) between the primary bag 3 and the mark A1, and the tube 16 also has an expanded part 165 (which has a larger outside diameter than the tube 16) between one end 162 thereof and the mark B2. These expanded parts 55 and 165 are easily visible so that correct connection is confirmed.

As mentioned above, the tubes 5 and 16 are connected to each other by cutting the tube 5 between the marks A1 and A2 and cutting the tube 16 between the marks B1 and B2 and then connecting the cut ends to each other such that the mark A1 adjoins the mark B1 and the mark A2 adjoins the mark B2. If adequate connection is made in the blood treatment circuit 200, the expanded parts 55 and 165 should be at both sides of the filter 15 or at the up-stream side adjacent to the inlet 151 and at the down-stream side adjacent to the outlet 152. If the tubes 5 and 16 are connected to each other in a reverse direction by mistake such that the mark A1 adjoins the mark B2 and the mark A2 adjoins the mark B1, then the expanded parts 55 and 165 exist only on the tube leading to the outlet 152 of the filter 15. Thus, this arrangement permits one to easily and rapidly judge whether or not adequate connection has been made (or the blood treatment circuit 200 has been assembled correctly) by observing the position of the expanded parts 55 and 165 after the tubes 5 and 16 have been connected to each other to assemble the blood treatment circuit 200.

Incidentally, the expanded parts 55 and 165 on the tubes 5 and 16 may be placed at any other positions than shown in FIG. 6. For example, the expanded parts 55 may be placed between the marks A2 and the secondary bag 7, and the expanded part 165 may be placed between the mark B1 and one end 161 of the tube 16.

The expanded parts to indicate correct connection are not restricted to those illustrated above. They may be replaced by those marks similar to the marks A1, A2, B1, and B2, or by tags or any objects that can be recognized visually or tactually.

Figure 8:
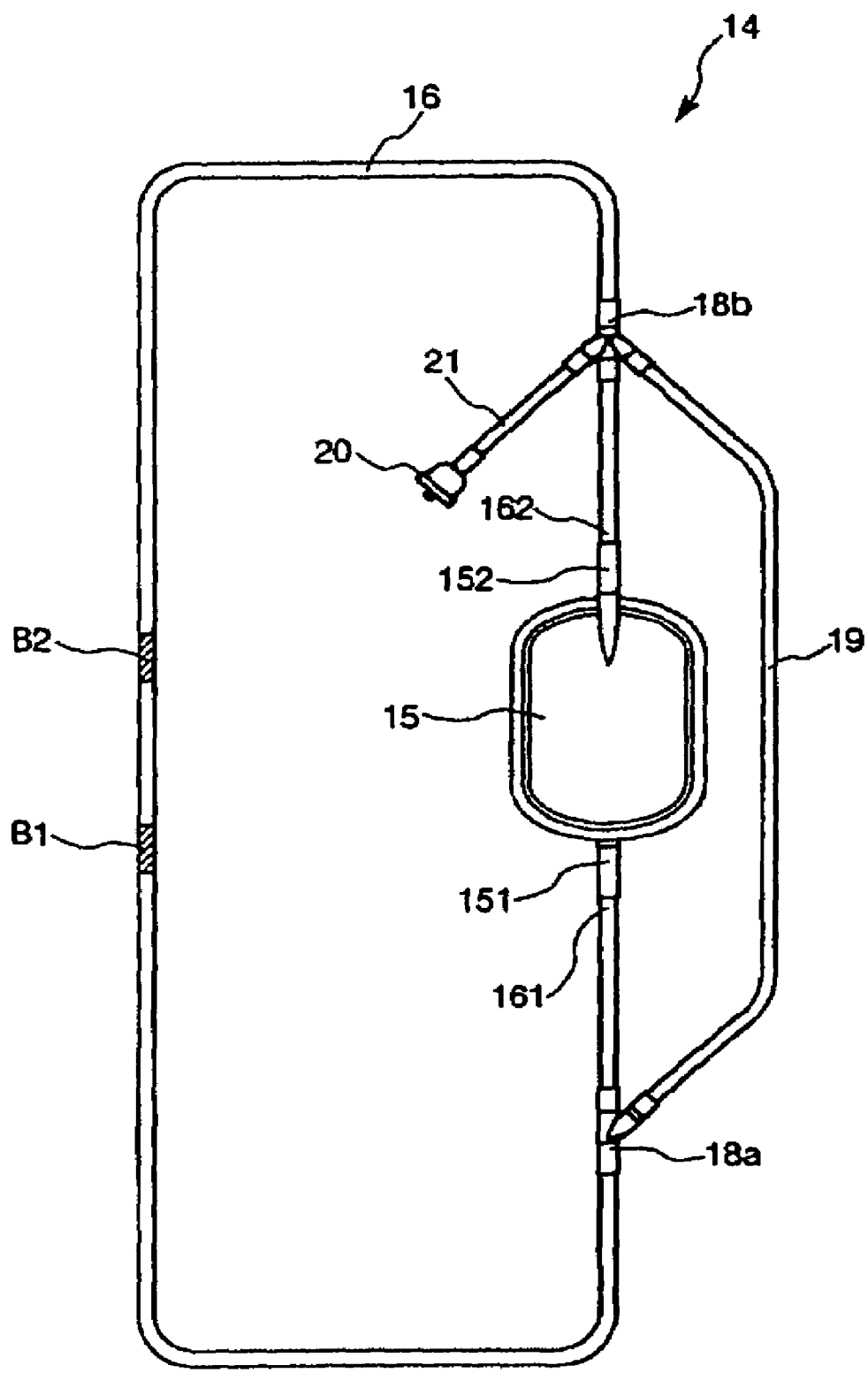
FIG. 8 is a schematic plan view showing a filter unit in another embodiment of the present invention.

FIG. 8 is a schematic plan view showing the filter unit according to another embodiment of the present invention. This filter unit 14 is identical with that in each of the above-mentioned embodiments except that it has a by-pass tube 19 that goes around the filter 15 and also has an air vent 20.

That is, the tube 16 has the branching connector 18a near its one end 161 and the branching connector 18b near its other end 162. The by-pass tube 19 is connected to the tube 16 through the branching connectors 18a and 18b to which both ends of the by-pass tube 19 are connected.

To the branching connector 18b is connected to the air vent 20 through the tube 21. Incidentally, the air vent 20 like this may be placed anywhere along the tube 16 or 19.

The filter unit 14 according to this embodiment, which has the by-pass tube 19 and the air vent 20, permits air which has entered the secondary bag 9 to be easily deaerated from the filter 15.

In addition, the air vent 20 admits gas or heat into the filter unit 14 at the time of sterilization. This ensures rapid sterilization of the filter medium in the filter unit 14.

The filter unit 14 constructed as shown in FIG. 8 may be applied to any one of the embodiments shown in FIGS. 1 to 7 above.

Figure 9A:
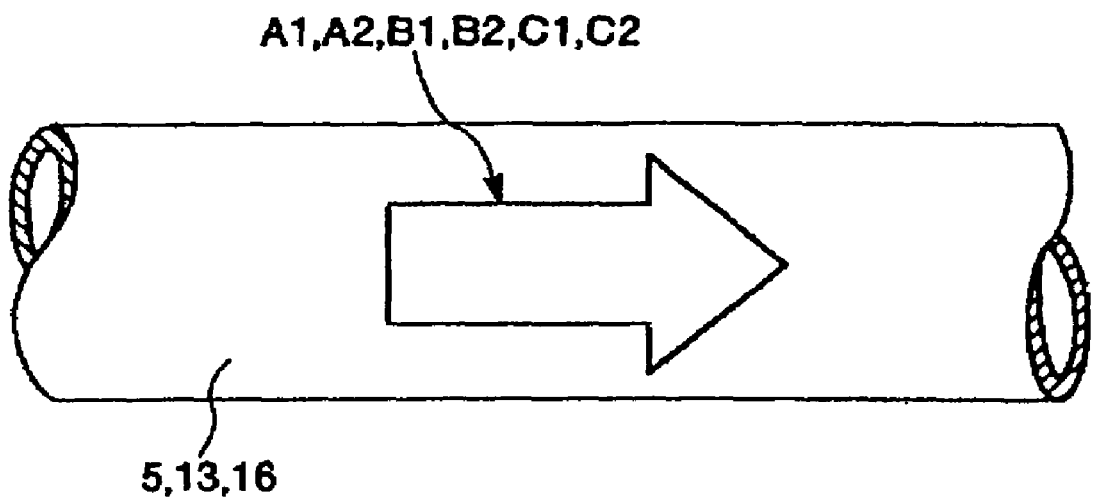
FIGS. 9A and 9B are plan views showing examples of marks attached to the tube.
Figure 9B:
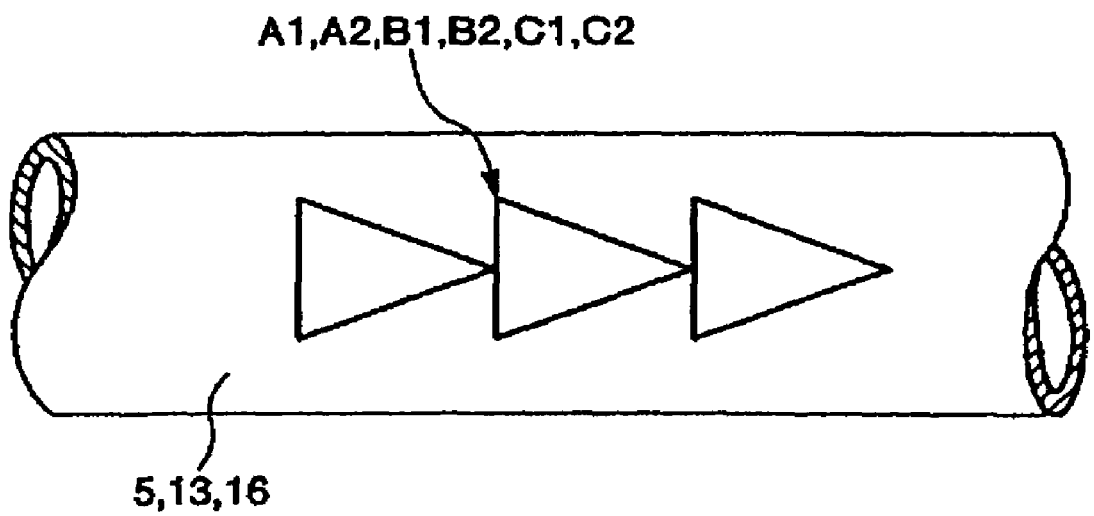

FIGS. 9A and 9B are plan views showing other examples of the mark placed on the tube. The marks A1, A2, B1, B2, C1, and C2 on the tubes 5, 13, and 16 may be an arrow shape, as shown in FIG. 9A, or may be made of more than one triangle, as shown in FIG. 9B. These marks indicate the direction of flow of fluids in the tubes 5, 13, and 16. These marks help make correct connection and ensure that correct connection has been made.

The marks A1, A2, B1, B2, C1, and C2 shown in FIGS. 9A and 9B may be distinguished from one another by coloring them differently or by identifying them with different letters.

In the foregoing, the present invention has been described with reference to the illustrated embodiments. However, the present invention is not restricted to such embodiments. The constitution of each part may be replaced by any equivalent one or may be supplemented with any constitution. In addition, more than one feature of the embodiments may be combined with one another.

In each of the above-mentioned embodiments, the connected bag set 1 includes four bags, one primary bag and three secondary bags. However, this constitution may be modified such that the connected bag set 1 includes two bags, one primary bag and one secondary bag, three bags, one primary bag and two secondary bags, or five or more bags, one primary bag and four or more secondary bags. There are no specific restrictions on the structure and use of the individual bags constituting the connected bag set.

Moreover, in each of the above-mentioned embodiments, one filter unit is incorporated into the connected bag set. However, the present invention is not limited to this constitution. More than one filter unit may be incorporated into the connected bag set. In this case the filter units may be of the same or different structure and may be incorporated into any place.

Moreover, in each of the above-mentioned embodiments, it is assumed that the filter unit has a filter medium to remove specific components (such as white blood cells) from blood (whole blood). However, the filter unit according to the present invention is not limited to the one mentioned above. It may be intended to treat any fluids containing blood components (such as concentrated red blood cells and concentrated platelets) or tissue-derived cells (such as cord blood, bone marrow fluid, and gene recombination cells). Moreover, these fluids may additionally contain physiological fluids, such as physiological saline, anticoagulant, preserving solution, nutrient solution, culture medium, and cytokine solution (culture promoting solution).

The filter unit according to the present invention treats fluids containing tissue-derived cells or gene recombination cells in the following manner.

(1) Treatment of whole blood or blood components is accomplished by removing at least one component (listed below)

and recovering remaining blood components. White blood cells (at least one of monocyte, granulocyte, and lymphocyte), platelet, red blood cell, aggregate, protein, prion, cytokine, endotoxin, bacteria, virus, and ion.

(2) Treatment of cord blood or bone marrow fluid is accomplished by capturing white blood cells and removing the remainder, or by removing at least one component (listed below) and recovering remaining components. Platelet, red blood cells, aggregate, tissue pieces, protein, cytokine, endotoxin, bacteria, virus, and ion.

(3) Treatment of fluids containing gene recombination cells is accomplished by removing at least one component (listed below) and recovering remaining components. Cells, aggregate, protein, cytokine, endotoxin, bacteria, virus, and ion.

(4) Treatment of fluids containing cytokine (to culture tissue-derived cells) is accomplished by capturing tissue-derived cells and removing remaining components or by removing at least one component (listed below) and recovering remaining components. Aggregate, tissue pieces, protein, cytokine, endotoxin, bacteria, virus, and ion. Each treatment employs a cell treatment set including an apparatus to hold treated fluids and an apparatus to treat cells.

INDUSTRIAL APPLICABILITY

According to the present invention, the blood treatment circuit is assembled by aseptically connecting a sterilized and closed filter unit to a sterilized and closed connected bag set. Blood treatment is performed by connecting the filter unit only when it is necessary to remove specific components from blood, to thereby obtain optimum products. Moreover, the blood treatment circuit permits the filter and the connected bag to be sterilized separately by the most suitable method under the most suitable condition. This contributes to the improved filter performance. Thus the present invention has a high is potential for industrial use.

The invention claimed is:

1. A method for assembling a blood treatment circuit by aseptically connecting a connected bag set, which has previously been sterilized, and a filter unit, which has previously been sterilized, to each other, said connected bag set being composed of a primary bag holding collected blood and a plurality of secondary bags holding blood or blood components and a first tube to connect said primary bag to said secondary bags and a third tube to connect said secondary bags to one another, said filter unit having an inlet and an outlet, a filter medium to remove specific components from a fluid introduced through said inlet, and a second tube, both ends of which are connected to said inlet and said outlet, and to which a bag is not connected, wherein said method comprises:
cutting either said first tube or said third tube so that either said first tube or said third tube comprises first and second cut ends;
cutting said second tube so that the second tube comprises first and second cut ends;
aseptically connecting said first cut end of said first tube or said third tube to said first cut end of said second tube, and connecting said second cut end of said first tube or said third tube to said second cut end of said second tube, thereby placing said filter unit along said first tube or said third tube.

2. The method for assembling a blood treatment circuit as defined in claim 1, wherein said first tube or said third tube has a mark that indicates the position of its connection to the second tube.

3. The method for assembling a blood treatment circuit as defined in claim 2, wherein said mark indicates the direction of flow of fluid in the tube.

4. The method for assembling a blood treatment circuit as defined in claim 1, wherein said tube has a mark indicating that the second tube has been correctly connected to the first tube or the third tube.

5. The method for assembling a blood treatment circuit as defined in claim 4, wherein said mark is comprised of an expanded outside diameter of the second tube.

6. The method for assembling a blood treatment circuit as defined in claim 1, wherein said connected bag set and said filter unit are sterilized in different manners or under different conditions.

7. The method for assembling a blood treatment circuit as defined in claim 6, wherein said connected bag set is sterilized by moist heat sterilization and said filter unit is sterilized by gas sterilization or radiation sterilization.

8. The method for assembling a blood treatment circuit as defined in claim 1, wherein said second tube has a mark that indicates the position of its connection to said first tube or the third tube.

9. The method for assembling a blood treatment circuit as defined in claim 8, wherein said mark indicates the direction of flow of fluid in the tube.

10. A method for assembling a blood treatment circuit, said method comprising:
sterilizing a connected bag set which is composed of a primary bag holding collected blood and a plurality of secondary bags holding blood or blood components, a first tube to connect said primary bag to said secondary bags, and a third tube that connects said secondary bags to one another;
sterilizing a filter unit having an inlet and an outlet, a filter medium to remove specific components from a fluid introduced through said inlet, and a second tube both ends of which are connected to said inlet and said outlet; and to which a bag is not connected; and
cutting either said first tube or said third tube so that either said first tube or said third tube comprises first and second cut ends;
cutting said second tube so that the second tube comprises first and second cut ends;
aseptically connecting said first cut end of said first tube or said third tube to said first cut end of said second tube, and aseptically connecting said second cut end of said first tube or said third tube to said second cut end of said second tube, thereby placing said filter unit along said first tube or said third tube.

11. The method for assembling a blood treatment circuit as defined in claim 10, wherein said second tube or said third tube has a mark that indicates the position of its connection to the second tube.

12. A blood treatment circuit assembled by aseptically connecting a filter unit to a connected bag set, said connected bag set having previously been sterilized and being composed of a primary bag holding collected blood and a plurality of secondary bags holding blood or blood components and a first tube to connect said primary bag to said secondary bags and a third tube to connect said secondary bags to one another, said filter unit comprising an inlet and an outlet, a filter medium to remove specific components from fluid introduced through said inlet, and a second tube, both ends of which are connected to said inlet and said outlet, and to which a bag is not connected,
wherein either said first tube or said third tube is aseptically connected to said second tube by using an apparatus for aseptically connecting tubes, and wherein said apparatus for aseptically connecting said first tube or said third tube to said second tube cuts said first tube or said third tube, and said second tube, and then aseptically connects one of said first tube and said third tube, to said second tube at their cut surfaces, such that one of said cut surfaces of said first tube or said third tube facing one direction is connected to one of said cut surfaces of said second tube facing an opposite direction, whereas the other of said cut surfaces of said first tube or said third tube facing said opposite direction is connected to the other of said cut surfaces of said second tube facing said one direction, thereby placing said filter unit along said first tube or said third tube.

13. The blood treatment circuit as defined in claim 12, wherein said second tube has a mark that indicates the position of its connection to said first or said third tube.

14. The blood treatment circuit as defined in claim 13, wherein said mark indicates the direction of flow of fluid in the second tube.

15. The blood treatment circuit as defined in claim 12, wherein said second tube has a mark indicating that the second tube has been correctly connected to the first tube or the third tube.

16. The blood treatment circuit as defined in claim 15, wherein said mark is comprised of an expanded outside diameter of the second tube.

17. The blood treatment circuit as defined in claim 12, said filter unit having a by-pass tube that goes around said filter medium.

18. The method for assembling a blood treatment circuit as defined in claim 12, wherein the connected bag set is a moist heat sterilized connected bag set, and the filter unit is not a moist heat sterilized filter unit.

19. The method for assembling a blood treatment circuit as defined in claim 12, wherein the connected bag set is a moist heat sterilized connected bag set, and the filter unit is a gas sterilized filter unit or a radiation sterilized filter unit.

20. A blood treatment circuit assembled by:
sterilizing a connected bag set composed of a primary bag holding collected blood and a plurality of secondary bags holding blood or blood components, a first tube connecting said primary bag to said secondary bags, and a third tube connecting said secondary bags to one another;
sterilizing a filter unit having an inlet and an outlet, a filter medium to remove specific components from a fluid introduced through said inlet, and a second tube having ends connected to said inlet and said outlet, and to which a bag is not connected;
cutting either said first tube or said third tube so that either said first tube or said third tube comprises first and second cut ends;
cutting said second tube so that the second tube comprises first and second cut ends; and
aseptically connecting said first cut end of said first tube or said third tube to said first cut end of said second tube, and aseptically connecting said second cut end of said first tube or said third tube to said second cut end of said second tube so that the filter unit is positioned along said first tube or said third tube.

21. The blood treatment circuit as defined in claim 20, wherein said second tube has a mark indicating the position of its connection to said first tube or said third tube.

22. The blood treatment circuit as defined in claim 21, wherein said mark indicates the direction of flow of fluid in the second tube.

23. The blood treatment circuit as defined in claim 20, wherein said second tube has a mark indicating that the second tube has been correctly connected to the first tube or the third tube.

24. The method for assembling a blood treatment circuit as defined in claim 20, wherein said first tube or said third tube has a mark indicating a position of its connection to said second tube.

25. The method for assembling a blood treatment circuit as defined in claim 20, wherein the connected bag set is a moist heat sterilized connected bag set, and the filter unit is not a moist heat sterilized filter unit.

26. The method for assembling a blood treatment circuit as defined in claim 20, wherein the connected bag set is a moist heat sterilized connected bag set, and the filter unit is a gas sterilized filter unit or a radiation sterilized filter unit.

* * * * *